United States Patent [19]

Jacquier et al.

[11] Patent Number: 5,077,387
[45] Date of Patent: Dec. 31, 1991

[54] PROCESS FOR PREPARING PEPTIDE SYNTHONS

[75] Inventors: Robert Jacquier, Montpellier; Jean Verducci, Baillargues; Michel Ibea, Montpellier, all of France

[73] Assignee: Rhone-Poulenc Chimie, Courbevoie Cedex, France

[21] Appl. No.: 188,488

[22] Filed: Apr. 29, 1988

[30] Foreign Application Priority Data

Nov. 25, 1987 [FR] France ................................ 87 16341

[51] Int. Cl.$^5$ ............................ C07K 1/02; C07K 1/06
[52] U.S. Cl. .................................... 530/335; 530/334; 530/338
[58] Field of Search ........................ 530/334, 335, 338

[56] References Cited

U.S. PATENT DOCUMENTS 4,725,645 2/1988 Anteunis et al. ..................... 530/334

FOREIGN PATENT DOCUMENTS 0184243 6/1986 European Pat. Off. .
0289353 11/1988 European Pat. Off. ............ 530/334

OTHER PUBLICATIONS

Fournier, A., et al., *Int. J. Peptide Protein Res.*, 31:86–97, 1988.
Vanfleteren, L., et al., *Bull. Soc. Chem. Belg.*, 97:505–517, 1988.
Tung, R., et al., *J. Org. Chem.*, 51:3350–3354, 1986.
Kricheldorf, H., *Liebigs Ann. Chem.*, 763:17–38, 1972.
Miyazawa et al., Peptide Chemistry, 1982, pp. 69–74.
Arnold et al., Synthetic Reactions of Dimethylformamide XIV., 1961.

*Primary Examiner*—Howard E. Schain
*Assistant Examiner*—Susan M. Perkins
*Attorney, Agent, or Firm*—Finnegan, Henderson, Farabow, Garrett and Dunner

[57] ABSTRACT

The present invention relates to a process for preparing peptide synthons in which the optical purity of each of the peptides to be condensed is retained.

According to this process, a silyl derivative of an amino acid or peptide, which is activated by a complex chloroimmonium salt, a complex coordinated phosphorus halide, oxyhalide salt or a complex oxalyl halide salt, is prepared. The activated peptide is then condensed with an N-silyl amino acid or peptide in which the acid group is protected.

13 Claims, No Drawings

PROCESS FOR PREPARING PEPTIDE SYNTHONS

BACKGROUND OF THE INVENTION

The present invention relates to a process for preparing peptide synthons. It relates more especially to a new method of a non-racemizing peptide synthesis.

It is known from certain specialized works, such as, for example, The Peptides, vol. 1, Academic Press (1979), or Principles of Peptide Synthesis, Springer (1984) to carry out peptide syntheses by condensing a peptide chain in which the acid terminus is activated (E) and the amine terminus is protected (P) with another peptide chain in which only the acid terminus is esterified. This synthesis is carried out in the presence of an organic base which permits neutralization of the leaving group (EOH) which is in most cases acidic. This synthesis is performed by the following reactions:

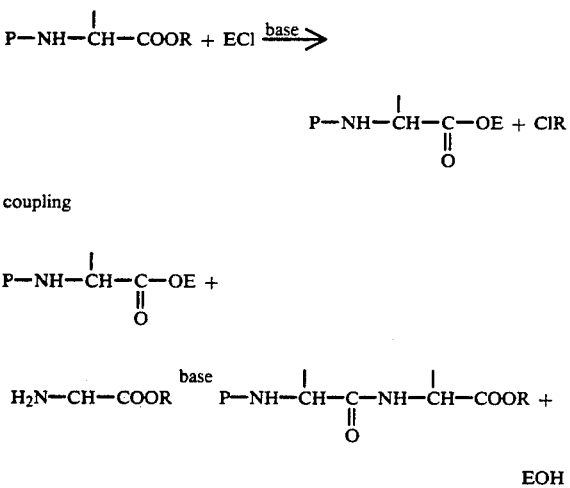

The base used, irrespective of its nature, causes substantial racemization of the peptide unit, either during the activation stage or during the coupling stage.

It is well known in peptide synthesis that most peptides are active only under a single diastereoisomeric form. Racemization causes a loss of activity of the products obtained after the condensation. This racemization is very detrimental to the use of the peptides because the chirally active starting materials used are often very expensive. Since the peptides are used in the pharmaceutical industry, which sets stringent analytical standards, the peptides must be purified if their synthesis produces a mixture of diastereoisomers. This purification is very costly.

As a result, industry has been seeking for a long time chemical processes which compete with the processes of extraction from natural products. Industry as sought active peptides of well defined chiral purity at a cost capable of competing with the extraction processes.

It is known, for example, to prepare peptides while inhibiting racemization to a maximum by the use of activating agents such as dicyclohexylcarbodiimide (DCC) and additives such as:
N-hydroxysuccinimide,
1-hydroxybenzotriazole,
N-hydroxy-5-norbornene-2,3-dicarboximide.

It is generally known to condense, without excessive racemization, amino acids which are N-protected by urethane groups. This condensation is performed by a synthesis technique that enables amino acids to be added to a peptide one by one. On the other hand, when the amine group is substituted by an acyl group, as disclosed by Miyazawa, Yamada and Kuwata, Peptide Chemistry, 69 (1982), or it forms part of a peptide chain, the degree of racemization is no longer insignificant and can reach 25%.

It is also known, from European Patent No. 184,243, to prepare silyl derivatives of amino acids or peptides using trialkylcyanosilanes, and then to couple these silyl derivatives with activated amino acids or peptides. During the silylation, there is a liberation of hydrocyanic acid, which is so toxic that it has led to the exclusion of this process from all industrial programs. Moreover, the activating agents used in the above-mentioned patent cannot be used on peptide fragments without the occurrence of substantial racemization.

Consequently, the degree of racemization varies with the amino acid, the protective group, the activating reagent and the conditions of the activation reaction. In particular, the degree of racemization can be complete when an acyl type protective group is used.

SUMMARY OF THE INVENTION

The present invention makes it possible to solve the problems remaining in the prior art. The present process can, by a chemical method using starting materials of low cost, produce peptide synthons possessing a chiral purity as high as equal to or greater than 99% on condensing or coupling. This chiral purity can be obtained, for example by coupling valine with another valine. Under experimentation conditions not in accord with the present invention, the coupling of valine with valine, for example, when activated with (i) DCC and an additive, (ii) pivaloyl chloride and a tertiary amine, or (iii) N-N'-bis(2-oxo-3-oxazolidinyl) phosphinyl chloride (BOP-Cl) and tertiary amine, leads to a not insignificant racemization.

The present invention provides a process for preparing an optically active peptide synthon. In particular, the present process can provide a substantially optically pure peptide synthon. In the first step, an oxygen-silyl derivative of a peptide or an amino acid, in which the nitrogenous group is protected, is prepared. In the second step, the oxygen-silyl peptide or amino acid is activated by a salt selected from the group consisting of complex chloroimmonium salts, complex coordinated phosphorus halide salts, such as phosphorus trichloride, oxyhalide salts, and complex oxalyl halide salts, such as oxalyl chloride salt. In a third step, the activated peptide or amino acid is condensed with a peptide or amino acid having an N-silylated amine group and a protected acid group. When the complex salt is based on antimony, an alkyl phosphite additive is used in the third step.

The present invention, hence, excludes all involvement of basic compounds, especially in the activation step and in the coupling or condensing step. This is especially advantageous when the starting material is an oxygen-silyl component containing more than one amino acid.

These and other features and advantages of the present invention will be made more apparent from the following description of the preferred embodiment.

DETAILED DESCRIPTION OF THE PREFERRED EMBODIMENT

Preferably, the overall reaction of the present invention can be represented schematically by the following reactions:

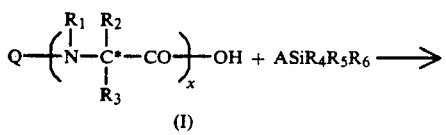  (A)

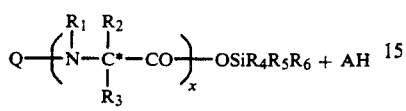

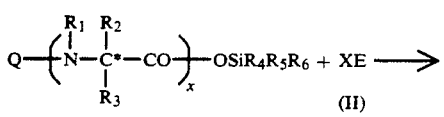  (B)

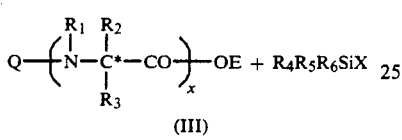

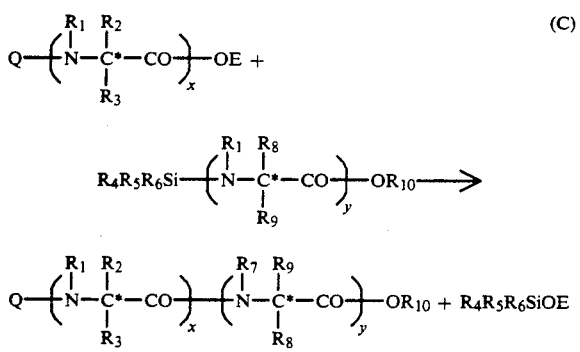  (C)

A in the formulae denotes chlorine or a group

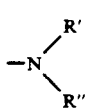

in which:

R' denotes hydrogen or an alkyl group $C_nH_{2n+1}$ with n being an integer between 1 and 4;

R'' denotes an alkyl group $C_nH_{2n+1}$ with n being an integer between 1 and 4, or a trialkylsilyl group in which the alkyl group contains 1 to 4 carbon atoms;

R' and R'' can also form an alkylsilyloxyalkylidene group, and in particular the group

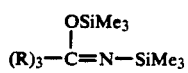

wherein R denotes a hydrogen or a fluorine atom.

Q is one of the protective groups for the N-terminal amine group used in the methods known in the prior art, such as Gross and Meienhofer, The Peptides, Vol. 3, Academic Press (1981). By way of non-limiting examples, Q can be a t-butyloxycarbonyl (BOC), benzyloxycarbonyl (Z), fluorenylmethyloxycarbonyl (Fmoc), benzoyl, trifluoroacetyl or a formyl group.

$R_1$ and $R_7$ are independently either hydrogen or a methyl group.

$R_2$ and $R_8$ may be chosen from the following substituents: hydrogen, alkenyl groups or alkyl groups having the formula $C_nH_{2n+1}$, either linear or branched, with n possessing integral values between 1 and 4, benzyl groups or one of the groups included in the non-limiting list appearing below:

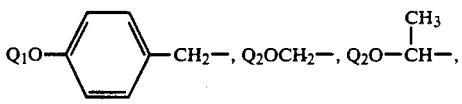

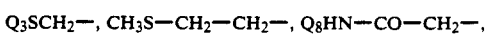

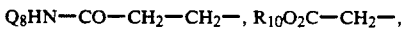

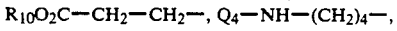

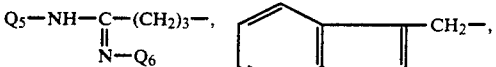

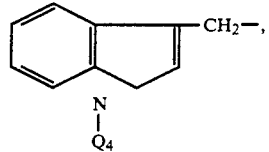

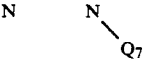

in which $Q_1$, $Q_2$, $Q_3$, $Q_4$, $Q_5$, $Q_6$, $Q_7$ and $Q_8$ are protective groups for the side chains, used in the methods disclosed in Gross and Meienhofer, The Peptides, Vol. 3, Academic Press (1981). By way of non-limiting examples, $Q_1$ can be a benzyl, 2-bromobenzyl or 2,6-dichlorobenzyl group; $Q_2$ a benzyl or t-butyl group; $Q_3$ a benzyl, t-butyl, trityl, acetamidomethyl or benzamidomethyl group; $Q_4$ a trifluoroacetyl, t-butyloxycarbonyl or benzyloxycarbonyl group; $Q_5$ can be a nitro, p-methoxybenzenesulfonyl or mesitylenesulfonyl group when $Q_6=H$, or alternatively $Q_5$ and $Q_6$ can simultaneously consist of an adamantyloxycarbonyl group; $Q_7$ can be a phenacyl, benzyloxymethyl or t-butoxymethyl group; and finally $Q_8$ can be a benzhydryl, dimethoxybenzhydryl or xanthydryl group.

$R_3$ and $R_9$ are independently chosen from the following substituents: hydrogen, or an alkyl group $C_nH_{2n+1}$, with n being an integer between 1 and 4.

$R_1$ with $R_2$ or $R_7$ with $R_8$ can also form a cyclopolymethylene chain containing 2 to 5 carbon atoms. The carbon atoms to which the substituents $R_2$ and $R_8$ are attached possess the L or D configuration. They are asymmetric (*) except when $R_2=R_3$ and $R_8=R_9$.

In the formula, x and y are integers between 1 and 15.

$R_4$, $R_5$ and $R_6$ are chosen from hydrogen and alkyl groups $C_nH_{2n+1}$, with n being an integer between 1 and 4, on condition that these three substituents are not simultaneously hydrogen atoms.

$R_{10}$ is one of the protective groups of the C-terminal acid group and of the side chain acid groups used in the methods disclosed by Gross and Meienhofer, The Peptides, vol. 3, Academic Press (1981). By way of non-limiting examples, $R_{10}$ may be methyl, ethyl, phenyl, benzyl or t-butyl groups.

XE denotes the activating reagent. The activating reagent (XE) is a salt chosen from complex chloroimmonium salts, complex coordinated phosphorus halide salts, oxyhalide salts, and complex oxalyl halide salts.

Preferably, the complex chloroimmonium salts correspond to the formula (IV):

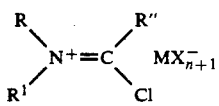
(IV)

in which:

X denotes a halogen chosen from chlorine, bromine and iodine;

R and R', which may be identical or different, denote an alkyl radical preferably having from 1 to 5 carbon atoms, or alternatively a divalent radical of the formula:

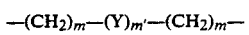

in which:

Y is a methylene group or a hetero atom such as an oxygen or nitrogen atom;

m is an integer from 2 to 6, and preferably equal to 2;

m' is an integer equal to 0 or 1;

R" is a hydrogen atom or an alkyl, alkenyl, aryl or aralkyl group;

M denotes a metal chosen from zinc, aluminum, antimony, titanium and tin;

n is an integer equal to or greater than 2 and equal to or less than 5.

Among the metals mentioned, it is preferable to use zinc and antimony V.

Preferably, the complex coordinated phosphorus halide salts correspond to the formula (V). These salts are new products not described in the prior art:

(V)

in which:

M denotes antimony when n=5 or zinc when n=2;

$X^1$ and $X^2$ denote an identical or different halogen chosen from chlorine, bromine or iodine.

The complex oxalyl halide salts are prepared in situ and are not isolated.

A process for preparing the complexes of formula (IV) is carried out by adding a metal halide to a chloroimmonium salt and, for the other complexes, by adding antimony V halide or zinc halide to the phosphorus halide or the oxalyl halide. The preparation process is preferably carried out at a temperature below 0° C.

These complexes are prepared in solvents chosen from halogenated aliphatic solvents, such as chlorinated aliphatic solvents, and preferably from methylene chloride and chloroform.

The silylation reaction of the acid group is preferably carried out, starting with an N-protected amino acid or peptide, by reaction with a silylating reagent of formula $ASiR_4R_5R_6$ in which the terms A, $R_4$, $R_5$ and $R_6$ have the same meaning as above.

The silylation reaction of the amine group is preferably carried out, starting with an amino acid or peptide, by reaction between a corresponding ester and a silylating reagent of formula $AsiR_4R_5R_6$ in which the terms A, $R_4$, $R_5$ and $R_6$ have the same meaning as above.

These silylation reactions are performed under the conditions known in the prior art.

The amino acid or peptide derivatives are introduced with the silylating agent into a solvent such as, for example, an ether (tetrahydrofuran), a halogenated aliphatic solvent, an ester, a nitrile (acetonitrile) or an amide (DMF).

According to one method, amino acid or peptide concentrations in the solvent of between 0.1 and 1 mole per liter are preferably used.

Concentrations of silylating agent with respect to the amino acid or peptide of between 1 and 3 moles are advantageously used.

For a particularly preferred embodiment of the invention, the second step of bringing a peptide or amino acid in which the amine group is protected and the acid group is oxygen-silylated into contact with a complex chloroimmonium salt of formula (IV), a complex coordinated phosphorus halide salt of formula (V), a oxyhalide salt or a complex oxalyl halide salt, is conducted under a stream of inert gas, such as nitrogen or argon, in a halogenated aromatic or aliphatic solvent. It is possible to use any solvent which permits solubilization of the activated peptide or amino acid and does not react either with the latter or with the salts. The solvent is chosen, in particular, from methylene chloride, chloroform, 1,2-dichloroethane and chlorobenzene.

It is preferable to use a quantity of salt such that the mole ratio of the complex chloroimmonium salt, the coordinated complex phosphorus halide, the oxyhalide salt, or the complex oxalyl halide salt to the activated peptide or the activated amino acid is between 1.1:1 and 1.3:1.

The reaction between the complex chloroimmonium salt, the coordinated complex phosphorus halide salt, the oxyhalide salt, such as phosphorus oxyhalide, or the complex oxalyl halide salt and the amino acid or peptide is preferably carried out at a temperature of between $-20°$ C. and $30°$ C. It is preferable to use a molar concentration of complex salt, amino acid or peptide in the solvent of between 0.01 and 0.1 mole/liter.

The time of the activation stage advantageously varies between 30 minutes and 2 hours.

As regards the coupling or condensing reaction of step (3), it is known in the prior art to couple or condense silyl derivatives to the carboxyl group and to the amino group. However, in none of these processes is there described coupling or condensing between a derivative activated by an immonium group or by the other salts mentioned above and a derivative silylated on the nitrogenous group. In point of fact, this very precise coupling or condensing brings about the altogether unexpected result of no racemization.

The coupling or condensing step is carried out by preferably adding the silylated amino or peptide compound to the solution of the activated peptide or amino acid under an inert gas atmosphere and preferably at a temperature of between $-10°$ C. and $30°$ C. When a complex antimony salt is used, it is advantageous to use an additive chosen from alkyl phosphites. It is preferable to use methyl phosphite, although other alkyl phosphites can also be used. Advantageously, a quantity of phosphite is added such that the mole ratio with respect to the activated amino acid or activated peptide is between 2 and 3.

Advantageously, with the complex phosphorus halide salts, the oxyhalide salts, and the complex oxalyl halide salts, it is possible to perform the activation and coupling stage simultaneously.

The time of the coupling step preferably varies between 5 hours and 24 hours.

The invention will be described more completely by means of the examples which follow, which must in no case be considered to limit the invention.

EXAMPLE 1

A solution of 1 ml (10 meq) of phosphorus trichloride in 8 ml of chloroform was placed in a three-necked round-bottomed flask equipped with a thermometer, a stirrer and an adding funnel and kept under nitrogen. The solution was cooled to $-20°$ C. and 2 ml (13 meq) of antimony pentachloride in 8 ml of chloroform were added dropwise with stirring. Upon completion of the addition, stirring was continued for 10 min at $-20°$ C., and then the reaction mixture was allowed to return to room temperature over the course of 1 hour. The solution was cooled to $-20°$ C. The precipitate was filtered and washed 3 times with small amounts of cold chloroform. The product was finally dried under vacuum without heating. The complex salt of formula (V) in which $M=Sb$, $n=5$ and $X=Cl$ melts at $105°-107°$ C. (90% yield).

EXAMPLE 2

0.732 g (2.5 meq) of trimethylsilyl ester of benzoyl-L-valine, 0.51 g (2.5 meq) of methyl ester of N-trimethylsilyl-L-valine and 1 ml (7.5 meq) of methyl phosphite were dissolved in 50 ml of methylene chloride. 1.31 g (3 meq) of complex salt obtained in Example 1 were added under nitrogen, and stirring was continued for 12 hours at room temperature. The product was filtered, washed three times with 1 N citric acid, three times with a saturated solution of sodium bicarbonate, once with water, and dried on magnesium sulfate. The solvent was evaporated off under vacuum.

The Bz-Val-Gly-OCH$_3$ dipeptide, which acts as a test for the determination of the yield in high performance liquid chromatography, was introduced before the washings.

The yield of Bz-Val-val-OCH$_3$ and the racemization level (expressed in DL %) were determined from the crude residue by reverse phase high performance liquid Chromatography, on a C 18 Ultrasphere Altex column, with a mixture of CH$_3$OH 52%—H$_2$O 48% as the eluant and a flow rate of 1 ml/min (254 nm detection).

65% yield DL %=0%.

EXAMPLE 3

The procedure of Example 2 was followed, but using the methyl ester of N-trimethylsilyl-L-proline as the amino component.

The yield of Bz-Val-Pro-OCH$_3$ and the racemization level were determined by reverse phase high performance liquid chromatography, on a C 18 Ultrasphere Altex column, with a mixture of CH$_3$OH 48%—H$_2$O 52% as the eluant and a flow rate of 1 ml/min.

55% yield DL %=1%.

EXAMPLE 4

0.42 ml (5 meq) of phosphorus trichloride and 0.952 g (7 meq) of dry zinc chloride were added successively under nitrogen to 1.02 g (5 meq) of methyl ester of N-trimethylsilyl-L-valine in 20 ml of methylene chloride. After 2 hours at 20° C., 0.732 g (2.5 meq) of trimethylsilyl ester of benzoyl-L-valine dissolved in 20 ml of methylene chloride was added. The mixture was finally stirred under nitrogen for 12 hours at 20°, and treated as indicated in Example 2.

67% yield DL=0%.

EXAMPLE 5

0.557 g (2.5 meq) of the beta-benzyl ester of N-tert-butyloxycarbonyl-L-aspartic acid and an excess of hexamethyldisilazane in 20 ml of anhydrous methylene chloride were stirred under nitrogen for 2 hours at room temperature. The reaction mixture was concentrated under vacuum without heating, and the residue was taken up with 50 ml of CH$_2$Cl$_2$. 0.63 g (2.5 meq) of methyl ester of N-trimethylsilyl-L-phenylalanine, 0.476 g (3.5 meq) of dry zinc chloride and 0.343 g (2.5 meq) of phosphorus trichloride were then added and stirred for 12 hours at room temperature under nitrogen. The product was filtered, washed three times with 1N citric acid, three times with a saturated solution of sodium bicarbonate, once with water, and dried on magnesium sulfate. The solvent was evaporated off under vacuum.

The yield of Boc-Asp (OBzl)-Phe-OCH$_3$ is 65%. Oil was defined by its NMR spectrum and by its mass spectrum.

The cleavage of the protecting group to yield Aspartame was finally carried out according to the procedures of the art. A catalytic reduction was carried out to remove the benzyl moiety from the aspartic acid, and the product was treated with trifluoroacetic acid in order to remove the Boc group.

EXAMPLE 6

The preparation of dimethylchloroimmonium (IV) hexachloroantimoniate was carried out following Arnold and Holy, 27 Coll. Czech. Chem. Comm. 2886 (1962).

A solution of 2.97 g of antimony pentachloride in 10 ml of chloroform was added dropwise with stirring at $-40°$ C. to 5 ml of a 2 M solution of dimethylchloroimmonium chloride in chloroform. The precipitate was filtered, washed twice with chloroform and dried. The melting point was $162°-164°$ C. with a 90% yield.

EXAMPLE 7

1.28 g (3 meq) of dimethylchloroimmonium (IV) hexachloroantimoniate ($R=R'=CH_3$, $R''=H$, $M=Sb$, $n=5$, $X=Cl$) were suspended under nitrogen in 50 ml of methylene chloride cooled to $-20°$ C. 0.732 g (2.5 meq) of trimethylsilyl ester of benzoyl-L-valine dissolved in 5 ml of CH$_2$Cl$_2$ was added dropwise with stirring. Upon dissolution of the reagent, stirring was continued another 30 min at $-20°$ C. 0.93 g (7.5 meq) of methyl phosphite was then added. After stirring for 15 min at $-20°$ C., 0.51 g (2.5 meq) of methyl ester of N-trimethylsilyl-L-valine was introduced still under nitrogen. The reaction mixture was stirred for 1 hour at $-20°$ C., and then allowed to return slowly to room temperature and stirred for 12 hours at 20° C. After filtration, the filtrate was washed 3 times with 1 N citric acid, twice with a saturated solution of sodium bicarbonate and once with water. The filtrate was dried on magnesium sulfate and the solvent was evaporated off under vacuum.

50% yield DL 0.2%

COMPARATIVE EXAMPLE 7

The procedure of Example 7 was followed, but without using methyl phosphite. The yield was approximately 20%. An accurate measurement of the DL was impossible and the yield was too low.

EXAMPLE 8

A mixture of 0.21 ml (2.5 meq) of oxalyl chloride and 0.44 ml (3.5 meq) of antimony pentachloride diluted in 2 ml of methylene chloride was added dropwise, under nitrogen, with stirring at 0° C. to a solution of 0.732 g (2.5 meq) of benzoyl-L-valine in 50 ml of methylene chloride. Stirring was continued for 1 hour at 20° C. 0.975 g (7.5 meq) of methyl phosphite was then added. After stirring for 5 min, 0.51 g (2.5 meq) of methyl ester of N-trimethylsilyl-L-valine was added. The mixture was finally stirred for 12 hours at 20° C., while still under nitrogen. The treatment was identical to that indicated in Example 2.

51% yield DL 0%.

EXAMPLE 9

0.44 g (5 meq) of dimethylformamide and 0.78 g (3.5 meq) of dry zinc bromide were dissolved in 30 ml of methylene chloride. The reaction mixture was cooled to $-20°$ C. and 0.25 ml (3 meq) of oxalyl chloride diluted in 5 ml of $CH_2Cl_2$ was added dropwise under nitrogen. After stirring for 30 minutes at $-20°$ C., 0.732 g (2.5 meq) of trimethylsilyl ester of benzoyl-L-valine in solution in 15 ml of methylene chloride was added dropwise with stirring. The mixture was stirred for 40 minutes while allowing the temperature to return slowly to 0° C. 0.51 g (2.5 meq) of methyl ester of N-trimethylsilyl-L-valine was then added, stirring was continued under nitrogen for 12 hours at room temperature, and the treatment procedure was as indicated in Example 2.

95–100% yield DL 0%.

While particular embodiments of the invention have been described, it will be understood that the invention is not so limited since many modifications and variations could be made without departing from the spirit or scope of the invention.

What is claimed is:

1. A process for preparing an optically active peptide synthon, comprising the steps of:
    (a) preparing an oxygen-silyl derivative of a peptide or amino acid in which at least an alpha-amino group is protected;
    (b) activating the oxygen-silyl peptide or amino acid with a salt selected from the group consisting of complex chloroimmonium salts, complex coordinated phosphorus halide salts, oxyhalide salts, and complex oxalyl halide salts; and
    (c) condensing the activated peptide or amino acid with a peptide or amino acid having a protected acid group and an N-silylated amino group;
    wherein said activating and condensing steps are performed in the absence of a base; and wherein when said slat is based on antimony an alkyl phosphate additive is used in the condensing step.

2. The process of claim 1, wherein the peptide synthon is substantially optically pure.

3. The process as claimed in claim 1, wherein the peptide of the first step contains more than two amino acids.

4. The process as claimed in claim 1, wherein the three steps are performed in the absence of a base.

5. The process as claimed in claim 1, wherein the complex coordinated phosphorus halide salt corresponds to the formula (V):

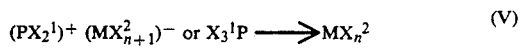

in which:
    M denotes antimony when n=5 or zinc when n=2;
    $X^1$ and $X^2$ denote an identical or different halogen chosen from chlorine, bromine and iodine.

6. The process as claimed in claim 1, wherein the complex salt is selected from the group consisting of phosphorus oxyhalide, oxalyl halide, zinc chloride and antimony pentachloride.

7. The process as claimed in claim 1, wherein the complex salt is selected from the group consisting of complex chloroimmonium salts, phosphorus trichloride salts, and oxalyl chloride salts.

8. The process as claimed in claim 7, wherein the mole ratio of the salt to the activated peptide or the activated amino acid is between 1.1:1 and 1.3:1.

9. The process as claimed in claim 1, wherein all the steps are carried out under a stream of inert gas and in the presence of an halogenated aromatic or aliphatic solvent.

10. The process as claimed in claim 9, wherein the solvent is selected from the group consisting of methylene chloride, chloroform, 1,2-dichloroethane and chlorobenzene.

11. The process as claimed in claim 1, wherein the second step is carried out at a temperature between $-20°$ C. and 30° C.

12. The process as claimed in claim 9, wherein the second step is carried out at a temperature between $-20°$ C. and 30° C.

13. The process as claimed in claim 1, wherein the second step is carried out in the presence of a solvent and the molar concentration of activated amino acid or activated peptide in the solvent is between 0.01 and 0.1 mole per liter solvent.

* * * * *

UNITED STATES PATENT AND TRADEMARK OFFICE
CERTIFICATE OF CORRECTION

PATENT NO. : 5,077,387
DATED : December 31, 1991
INVENTOR(S) : Robert Jacquier et al.

It is certified that error appears in the above-identified patent and that said Letters Patent is hereby corrected as shown below:

Claim 1, column 10, line 3, change "amino" to --amine--.

Claim 1, column 10, line 6, change "slat" to --salt--.

Claim 1, column 10, lines 6-7 change "phosphate" to --phosphite--.

Claim 12, column 10, line 48, change "claim 9" to --claim 5--.

Signed and Sealed this

Twenty-eighth Day of September, 1993

Attest:

BRUCE LEHMAN

Attesting Officer    Commissioner of Patents and Trademarks